United States Patent [19]

Franklin

[11] 3,965,123

[45] June 22, 1976

[54] MALEIC ANHYDRIDE RECOVERY

[75] Inventor: Frederick C. Franklin, Pinole, Calif.

[73] Assignee: Chevron Research Company, San Francisco, Calif.

[22] Filed: June 10, 1974

[21] Appl. No.: 477,556

[52] U.S. Cl. ........................................ 260/346.8 M
[51] Int. Cl.$^2$ ...................................... C07D 307/60
[58] Field of Search ................................ 260/346.8

[56] References Cited
UNITED STATES PATENTS
2,574,644   11/1951   Landau ........................... 260/346.8

FOREIGN PATENTS OR APPLICATIONS
869,297   5/1961   United Kingdom .............. 260/346.8

Primary Examiner—Harry I. Moatz
Attorney, Agent, or Firm—G. F. Magdeburger; John Stoner, Jr.; T. G. DeJonghe

[57] ABSTRACT

A process for recovery of good color stability maleic anhydride which comprises
a. removing maleic anhydride from a gaseous mixture containing maleic anhydride by absorption into an organic absorbent,
b. distilling maleic anhydride overhead from the resulting absorbent in a first distillation column,
c. condensing maleic anhydride out of the resulting overhead thereby obtaining condensed liquid maleic anhydride,
d. passing at least a portion of the condensed maleic anhydride to the upper part of a second distillation column, and
e. distilling material more volatile than maleic anhydride out of the condensed liquid maleic anhydride in a second distillation column, thereby obtaining stripped maleic anhydride which is withdrawn from the lower part of the second distillation column.

Preferably the stripped maleic anhydride is distilled in a third distillation column and purified maleic anhydride is withdrawn as an overhead product.

3 Claims, 1 Drawing Figure

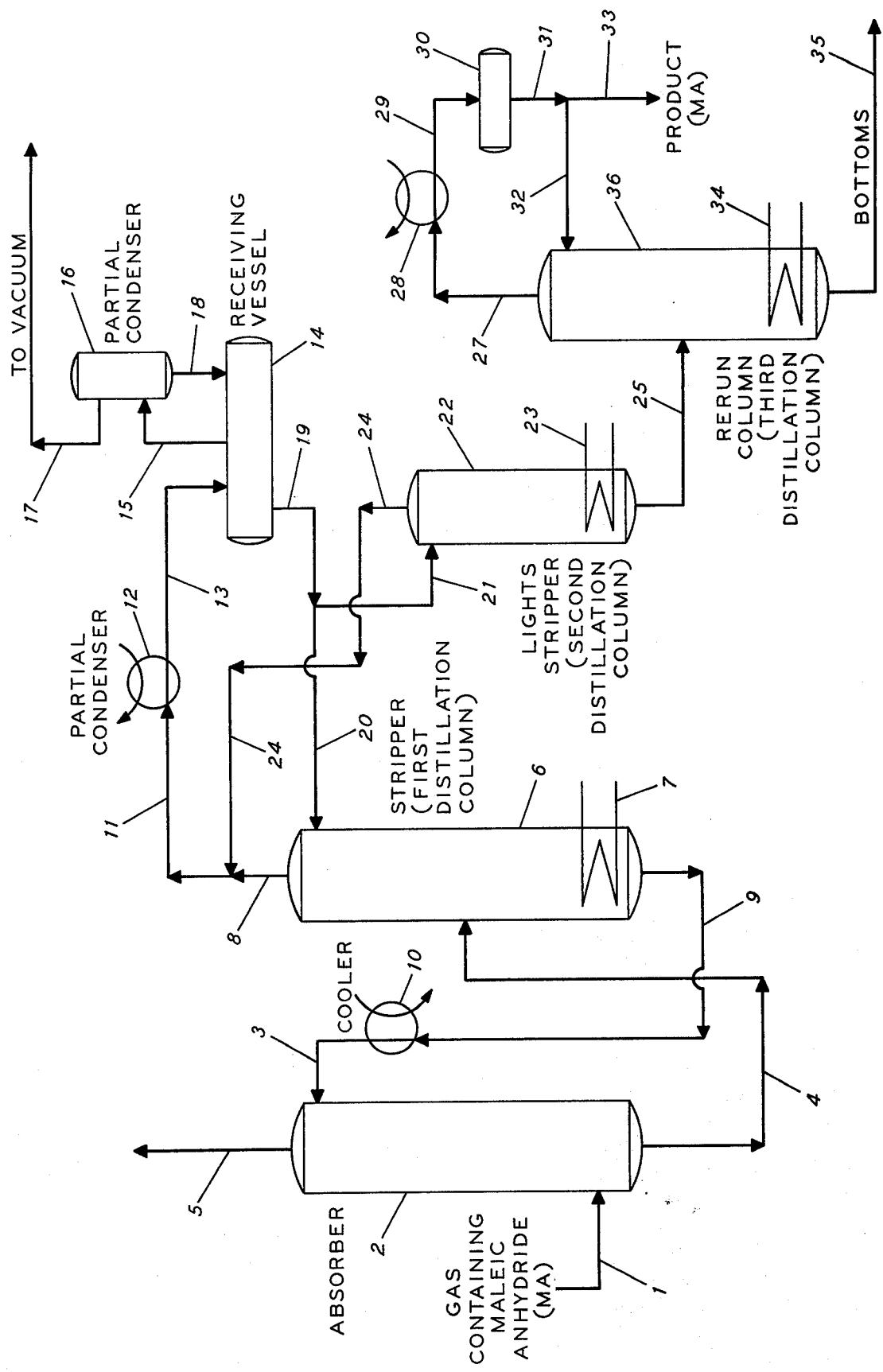

3,965,123

MALEIC ANHYDRIDE RECOVERY

BACKGROUND OF THE INVENTION

The present invention relates to the recovery of maleic anhydride from an organic absorbent. Maleic anhydride can be produced by vapor phase oxidation of a hydrocarbon feedstock in an oxidation reactor followed by recovery and then purification of the maleic anhydride. The most common feedstocks for maleic anhydride plants include benzene, butene and butane.

Recovery of the maleic anhydride from the gaseous effluent stream from the oxidation reactor can be done by scrubbing the effluent with water, which results in conversion of the anhydride to an acid. The acid then needs to be dehydrated to produce the anhydride product. Recovery of maleic anhydride from the oxidation reactor effluent using an organic absorbent as opposed to an aqueous absorbent has also been disclosed —for example, in U.S. Pat. Nos. 2,574,644; 2,893,924; 3,040,059; British Pat. No. 727,828 and Japanese Pat. Nos. 35-7460 and 32-8408. Commonly assigned U.S. patent applications Ser. Nos. 209,069; 310,320; and 427,177 also disclose organic absorbents for maleic anhydride recovery (removal), and the disclosures of the aforesaid patents and patent applications are incorporated herein by reference, particularly in their disclosure of various organic absorbents for recovery of maleic anhydride from gas streams containing maleic anhydride.

U.S. Pat. No. 2,574,644, in particular, discloses the use of dibutylphthalate for the recovery of maleic anhydride or phthalic anhydride from an oxidation reactor effluent stream. According to the process disclosed in U.S. Pat. No. 2,574,644 the oxidation reactor effluent is cooled to first condense a portion of the anhydride vapor. The remaining gaseous stream is contacted with the dibutylphthalate absorbent to remove the remaining uncondensed anhydride by absorption into the organic absorbent. The resulting rich absorbent is stripped to obtain a product anhydride stream.

The removal of maleic anhydride or phthalic anhydride from the organic absorbent in the process disclosed in U.S. Pat. No. 2,574,644 is carried out using a "rectifier" distillation column and a "stripper" distillation column. Basically the process is a two-stage stripping operation to thoroughly strip the anhydride out of the absorbent before the absorbent is reused for absorbing anhydride out of the oxidation reactor effluent gas stream containing the anhydride. Thus, after absorption of maleic anhydride into the absorbent in the absorber column, the anhydride-rich absorbent is passed to the first main stripper column, which is called a rectifier. A vacuum is pulled by a steam jet ejector off the top of the rectifier. The anhydride-rich absorbent stream is fed to the rectifier and the anhydride is stripped out of the absorbent by heat applied to the bottom of the rectifier column. The rectifier overhead is partially condensed to obtain liquid anhydride; part of which is returned to the rectifier as reflux and the other part of which is withdrawn as product anhydride.

Stripped absorbent in the U.S. Pat. No. 2,574,644 process is withdrawn from the bottom of the rectifier and passed to the upper part of a second distillation column, which is referred to as the stripper column. The stripper column is operated using a reboiler and a separate vacuum system so that the stripper column can be operated at a lower vacuum pressure than the rectifier. Thoroughly stripped absorbent is withdrawn from the bottom of the stripper column while a portion of the partially condensed overhead from the stripper is returned to the middle of the rectifier column.

SUMMARY OF THE INVENTION

According to the present invention a process is provided for recovery of good color stability maleic anhydride, which process comprises a. recovering maleic anhydride from a gaseous mixture containing maleic anhydride by absorption into an organic absorbent, b. distilling maleic anhydride overhead from the resulting absorbent in a first distillation column, c. condensing liquid maleic anhydride out of the resulting overhead thereby obtaining condensed liquid maleic anhydride, d. passing at least a portion of the condensed maleic anhydride to the upper part of a second distillation column, and e. distilling material more volatile than maleic anhydride out of the condensed maleic anhydride in a second distillation column, thereby obtaining stripped maleic anhydride which is withdrawn from the lower part of the second distillation column.

Preferably the stripped maleic anhydride is distilled in a third distillation column and purified maleic anhydride is withdrawn as an overhead product.

Among other factors, the present invention is based on the finding that the process sequence of the invention is highly effective in producing maleic anhydride product of good color stability; and furthermore, good color stability even when there is omitted the prior processing step of lagering, such as phosphorus pentoxide lagering, before final distillation. Lagering is a holding treatment at an elevated temperature, with or without added treating agents, before final distillation of the anhydride. British Pat. No. 1,204,846 and U.S. Pat. No. 3,564,022 are exemplary patents disclosing the use of substances such as various phosphorus oxides in the treatment of maleic anhydride to obtain maleic anhydride of good color stability.

Also the process of the present invention has been found to be advantageously used in continuous fashion rather than batch fashion to produce maleic anhydride. Previous batch processing involved taking a separate cut overhead from a column which might be comparable to the third distillation column of the present invention, such overhead cut being referred to as a forecut or heads cut. After the forecut, then the product heart cut of maleic anhydride would be taken overhead. The terminology "taken overhead" typically includes, of course, condensation of the overhead from a distillation column followed by removal of a liquid stream as the overhead product.

The process of the present invention has been found to produce maleic anhydride of good color stability without the forecut removal. In accordance with a preferred embodiment of the process of the present invention, the process is operated continuously as opposed to batchwise, and thus in accordance with this preferred embodiment no forecut removal is taken and/or no batchwise processing with a lagering step is used prior to distillation in the third distillation column. However, if desired, the process of the present invention can be operated batchwise with such added steps as lagering and/or taking of a forecut.

In accordance with a preferred embodiment of the present invention a single overhead receiving vessel is used for both the first and second distillation columns, the overhead from both said columns is partially condensed and fed to the receiving vessel, material more volatile than maleic anhydride is removed as a vapor stream from the receiving vessel, and a liquid stream of maleic anhydride is removed from the receiving vessel and distilled in the second distillation column to obtain stripped maleic anhydride in accordance with step (e).

BRIEF DESCRIPTION OF THE DRAWING

The drawing is a schematic process flow diagram illustrating a preferred embodiment of the present invention.

FURTHER DESCRIPTION OF THE DRAWING

Referring more particularly to the drawing, a gaseous mixture containing maleic anhydride is fed via line 1 to absorber 2. This gaseous mixture is generally sufficiently hot to be above the condensation point of any component in the mixture; in the case of maleic anhydride produced by air oxidation of a hydrocarbon, the condensation point is generally between about 200° and 250°F, depending on the pressure and the composition of the gas, particularly the water content. The gaseous mixture is typically generated by air oxidation of a hydrocarbon stream to produce a maleic anhydride as described in various prior art references on production of maleic anhydride. The gaseous mixture from the oxidation of the hydrocarbon is usually cooled to a temperature in the range 250°F to 350°F, preferably 270°–280°F, before it is fed to absorber 2.

In absorber 2, the maleic anhydride is scrubbed out of the gas mixture by an organic absorbent. The absorbent is introduced to the absorber via line 3, and flows downwardly in the absorber in countercurrent contact to the upwardly flowing gaseous mixture. By the time the gaseous mixture reaches the top of the absorber, it is substantially free of maleic anhydride (MA). The gas mixture exits via line 5. The MA-rich absorbent leaves the bottom of the absorber via line 4.

In stripper 6 the rich absorbent is stripped of the MA solute. The stripped MA product leaves the stripper via line 8. The stripping requires a heat input as indicated schematically by heater 7. The heat input is typically accomplished using a reboiler, although other conventional heating means can be used. Also the stripping can be accomplished using a hot stripping gas introduced as the lower part of the stripper. In general, operation of stripper 6 is in accord with conventional distillation procedures except for the overhead operation in association with the stripper. The purified absorbent resulting from the stripping can be termed "lean" absorbent. The lean absorbent is withdrawn from the bottom of stripper 6 via line 9. The lean absorbent can be and preferably is cooled, for example, as indicated by cooler 10 in the drawing, before the lean absorbent is introduced to the absorber via line 3.

The overhead maleic anhydride-rich vapor or gaseous stream from stripper 6 is passed via line 11 to partial condenser 12. The partial condenser condenses as liquid most of the maleic anhydride but leaves uncondensed some of the lighter gases such as acetic acid and water vapor. The condensed liquid anhydride along with uncondensed material more volatile than maleic anhydride is introduced via line 13 to receiving vessel 14. Receiving vessel 14 is operated under vacuum as is the stripper column itself. The vacuum can be drawn, for example, by a vacuum pump and is indicated as being drawn on the system via line 17. Volatile material is thus drawn off from the overhead system of the stripper via line 15, going into partial condenser 16 and then out of the overhead system via line 17. Partial condenser 16 operates to minimize maleic anhydride losses by condensing maleic anhydride out of the light material withdrawn from receiving vessel 14.

The condensed liquid maleic anhydride in receiving vessel 14 is passed via line 19 and then via line 20 into the stripper distillation column 6 as a reflux stream. Another portion of the line 19 material withdrawn from the receiving vessel is passed via line 21 to the top of "lights stripper" 22. The lights stripper thus operates on the product material itself and does not operate on the absorbent as in the case of the first distillation column—that is, stripper 6. Stripping is carried out in lights stripper 22 in accord with conventional distillation procedures—for example, using a reboiler as a heat source at the point indicated by heater 23 and using a cooling means at the top of the light stripper such as cool feed introduced via line 21. Light material stripped out of the maleic anhydride, such as acetic acid and/or acrylic acid, leaves the top of the lights stripper via line 24 and is then combined with the overhead from the first distillation column, as shown in the preferred schematic embodiment of the drawing.

Stripped maleic anhydride is withdrawn from the second distillation columm—that is, the lights stripper column—via line 25.

The stripped maleic anhydride is introduced to rerun column 36 and is distilled in accordance with conventional distillation procedures to obtain a purified overhead maleic anhydride product which is withdrawn via line 33. The overhead system of the rerun column includes condenser 28 and overhead receiving vessel 30. Reboiler or heating means for the rerun column are shown as indicated by heat source 34. Bottoms are withdrawn from the rerun column as indicated by line 35. The bottoms material can be separately distilled in a small batch still to maximize recovery of maleic anhydride as a distillate stream from a heavier residue. This recovered distillate can be recycled to the continuous system for repurification—for example, as part of the feed via line 21 to lights stripper 22.

EXAMPLES

EXAMPLE 1

Referring to FIG. 1, reactor gas obtained from the vapor-phase air oxidation of n-butane over a vanadium/phosphorus catalyst was charged to absorber 2 via line 1, at about 485 normal cubic feet per hour. The absorbent containing maleic anhydride was passed to the stripper column 6 via line 4. In the stripper maleic anhydride was stripped out of the absorbent. The stripped absorbent was recycled to the absorber, and the overhead crude maleic anhydride was passed from the stripper to receiving vessel 14 via lines 8, 11 and 13 at 12 cc per minute. This vessel was maintained at 190°F under a pressure of 50 mm. Crude maleic anhydride was removed from vessel 14 and charged to the lights stripper column 22 via lines 19 and 21 at a rate of 17 cc per minute. At the same time 7 cc per minute of crude maleic anhydride was fed back to the stripper via lines 19 and 20 to maintain reflux. The reboiler temperature in the lights stripper was held at 247°F. Volatile material, mainly maleic anhydride, was taken overhead from this distillation column at 236°F and was recycled back to vessel 14 via lines 24, 11, and 13 at a rate of 12 cc per minute. The stripped maleic anhydride from the lights stripper was removed through line 25 at a rate of 5 cc per minute. This product was saved in a storage vessel for further testing and/or purification. Under the above conditions maleic anhydride was produced at about 254 g per hour. In addition, 1.2 g per hour of low boiling material along with 3.3 g per hour of maleic anhydride was removed through lines 15 and 17.

EXAMPLE 2

Product Obtained Using Lights Stripper

A portion of the maleic anhydride product from the above-described storage tank was charged to a 20-sieve tray distillation column and was batch-distilled at 50 mm of pressure giving an overhead temperature of 238°F. The first 90% (weight of charge) of material distilled overhead was taken as the product cut. The remainder was left as bottoms. Manganous chloride, 1.0 ppm, was added to a portion of this distilled product to improve thermal stability. The stabilized product was then heated at 284°F for 24 hours. At the end of this time the color of the molten material was 20 to 50 Hazen, well below the average commercial level of about 80 Hazen.

Another portion of maleic anhydride from the storage tank was distilled as before except that the first 5% (by weight of charge) of distilled overhead was taken as a forecut. Then the next 85% of distilled material was taken as a product cut. Manganous chloride, 1.0 ppm, was added to a sample portion of the product cut. This sample was heated at 284°F for 24 hours and the color was then found to be 20 Hazen.

The above results indicate that maleic anhydride having outstanding color thermal stability is obtained by distilling maleic anhydride obtained from a lights stripper; and furthermore, all of the material distilled overhead is a satisfactory product; i.e., it is not necessary to take a forecut in the final or rerun distillation.

EXAMPLE 3

Product Obtained Without Lights Stripper

Crude maleic anhydride from receiving vessel 14 was charged to the same distilling apparatus as was used above, and a 5% (by weight of charge) forecut was removed. The remainder of the maleic anhydride was transferred to another vessel where it was mixed with 1.0% by weight of phosphorus pentoxide. The resulting mixture was heated and stirred at 295°F for 2 hours. It was then filtered and recharged to the same distillation apparatus as before. Then under the same conditions as described previously the first 85% of the distilled overhead material was taken as a product cut. A portion of this product cut was stabilized with 1.0 ppm of Manganous chloride, and the remainder was left unstabilized. Both samples were heated at 284°F for 24 hours. The stabilized sample had a color after 24 hours below the average commercial level of 80 Hazen, namely a color of about 10 Hazen The unstabilized sample had the same or worse Hazen color than did an unstabilized portion of the product from Example 2 (similarly heated for 24 hours at 284°F).

These results compared to the results of the previous example indicate that a phosphorus pentoxide treatment was not required in order to obtain maleic anhydride of good color thermal stability when utilizing a lights stripper in the maleic anhydride recovery and purification process in accordance with the present invention. Also, when utilizing the lights stripper much less than 5 weight percent of the charge to the lights stripper is taken out of charge. Thus, in the above examples only about 0.4 weight percent is taken out of the charge by distillation in the lights stripper whereas in the topping operation of Example 3 using phosphorus pentoxide, five weight percent is taken out by topping. Furthermore, the process of Example 2 is adaptable to continuous processing, having advantages of economy and ease of control to obtain consistent product quality compared to batch processing, whereas the process of Example 3 is inherently a batch process.

The following is a description of the "Hazen color" standard.

The color of molten maleic anhydride is measured by APHA color standards using standard platinum-cobalt solutions prepared in accordance with ASTM D-2280-66 procedure. This color scale was developed by the American Public Health Association and is also known as the Hazen Platinum Cobalt Scale. A description may be found at page 2048 of the 5th edition of "Standard Methods of Chemical Analysis," by wilford W. Scott.

Typical specifications on product maleic anhydride call for an APHA of Hazen color of 20 or lower for molten anhydride and a color of 40 or less after 2 hours' heating at 140°C (284°F). Good commercial maleic anhydride has a Hazen color below 125 after 24 hours at 140°C (284°F). Because the color of maleic anhydride is particularly prone to degrade (become darker) upon heating and because color tests frequently call for measurement after a prolonged period of heating, the color stability of maleic anhydride is also frequently referred to as color thermal stability.

What is claimed is:

1. A process for recovery of good color stability maleic anhydride which comprises:
   a. removing maleic anhydride from a gaseous mixture containing maleic anhydride by absorption into an organic absorbent, which absorbent is effective for maleic anhydride absorption and frees maleic anhydride upon distillation,
   b. distilling maleic anhydride overhead from the resulting absorbent in a first distillation column by applying heat to the absorbent at the bottom of the first distillation column,
   c. condensing liquid maleic anhydride out of the resulting overhead by cooling the resulting overhead in a partial condenser thereby obtaining condensed liquid maleic anhydride which is received in a receiving vessel separate from the condenser.
   d. passing at least a portion of the condensed liquid maleic anhydride from the receiving vessel to the upper part of a second distillation column,
   e. distilling material more volatile than maleic anhydride out of the condensed liquid maleic anhydride in the second distillation column by applying heat to bottoms material in the second distillation column, thereby obtaining stripped maleic anhydride which is withdrawn from the lower part of the second distillation column, and vapors which are which are withdrawn from the top of the second distillation column, and
   f. condensing liquid maleic anhydride out of said vapors by cooling said vapors in said partial condenser thereby obtaining condensed liquid maleic anhydride which is received in said receiving vessel, and g. passing at least a portion of the condensed maleic anhydride from step (f) to the first distillation column.

2. A process in accordance with claim 1 wherein the stripped maleic anhydride is distilled in a third distillation column and purified maleic anhydride is withdrawn as an overhead product.

3. A process in accordance with claim 2 wherein the maleic anhydride is withdrawn continuously as an overhead product.

* * * * *